United States Patent
Schilling et al.

(10) Patent No.: US 12,048,843 B2
(45) Date of Patent: Jul. 30, 2024

(54) METHOD FOR MINIMIZING MISALIGNMENT NOTIFICATIONS FOR A TRANSCUTANEOUS ENERGY TRANSFER SYSTEM

(71) Applicant: Medtronic, Inc., Minneapolis, MN (US)

(72) Inventors: Eric A. Schilling, Ham Lake, MN (US); Brian D. Kuhnley, Delano, MN (US); Erin N. Reisfeld, Minneapolis, MN (US); Stephen M. Nelson, Plymouth, MN (US); Nathanael O. Mason, Holliston, MA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 18/066,748

(22) Filed: Dec. 15, 2022

(65) Prior Publication Data
US 2023/0117943 A1   Apr. 20, 2023

Related U.S. Application Data

(63) Continuation of application No. 16/816,392, filed on Mar. 12, 2020, now Pat. No. 11,547,847.

(51) Int. Cl.
*A61M 60/148*   (2021.01)
*A61M 60/871*   (2021.01)
*H02J 50/10*   (2016.01)

(52) U.S. Cl.
CPC ............ *A61M 60/871* (2021.01); *H02J 50/10* (2016.02); *A61M 2205/18* (2013.01);
(Continued)

(58) Field of Classification Search
CPC ............ A61M 60/871; A61M 2205/18; A61M 2205/3368; A61M 2205/502;
(Continued)

(56) References Cited

U.S. PATENT DOCUMENTS

| 7,997,854 B2 | 8/2011 | LaRose et al. |
| 8,419,609 B2 | 4/2013 | Shambaugh, Jr. et al. |
| 9,707,327 B2 | 7/2017 | Heilman et al. |
| 10,193,395 B2 | 1/2019 | Bluvshtein et al. |

(Continued)

FOREIGN PATENT DOCUMENTS

WO    2015021493 A1    2/2015

OTHER PUBLICATIONS

International Search Report and Written Opinion of International Application No. PCT/US2021/016992, dated May 21, 2021, 10 pp.
Prosecution History from U.S. Appl. No. 16/816,392, now U.S. Pat. No. 11,547,847, dated May 25, 2022 through Sep. 20, 2022, 51 pp.

*Primary Examiner* — Abdul-Samad A Adediran
(74) *Attorney, Agent, or Firm* — Shumaker & Sieffert, P.A.

(57) ABSTRACT

A system for minimizing misalignment notifications for a TETS having an implantable blood pump, an external controller having a power source and a processing circuitry, a transmission coil in communication with the external controller, a receiving coil configured for transcutaneous inductive communication with the transmission coil, and an implantable controller in communication with the receiving coil and the implantable blood pump. The implantable controller having a power source configured to receive power from the receiving coil. The processing circuitry may be configured to: operate in a first mode where an alert is generated when a power efficiency transfer between the transmission coil and the receiving coil is below a first predetermined threshold; and operate in a second mode where the alert is only generated when the power remaining (Continued)

in the power source for the implantable controller is below a first predetermined power source threshold.

20 Claims, 4 Drawing Sheets

(52) U.S. Cl.
CPC ............... *A61M 2205/3368* (2013.01); *A61M 2205/502* (2013.01); *A61M 2205/8243* (2013.01); *A61M 2209/088* (2013.01)

(58) Field of Classification Search
CPC .... A61M 2205/8243; A61M 2209/088; A61M 60/875; H02J 50/10; H02J 50/12
USPC ...................................................... 600/16, 17
See application file for complete search history.

(56) References Cited

U.S. PATENT DOCUMENTS

| | | |
|---|---|---|
| 2006/0247737 A1 | 2/2006 | Olson et al. |
| 2010/0063347 A1* | 3/2010 | Yomtov .................. H02J 50/12 600/17 |
| 2011/0160516 A1 | 6/2011 | Dague et al. |
| 2012/0154143 A1 | 6/2012 | DAmbrosio |
| 2015/0196709 A1 | 7/2015 | Jacobson et al. |
| 2015/0290379 A1 | 10/2015 | Rudser et al. |
| 2016/0022889 A1* | 1/2016 | Bluvshtein .......... A61M 60/875 600/16 |
| 2016/0199556 A1 | 7/2016 | Ayre et al. |
| 2017/0246366 A1 | 8/2017 | Rudser |
| 2017/0304515 A1 | 10/2017 | Heilman et al. |
| 2019/0255237 A1 | 8/2019 | Cinbis |
| 2019/0290819 A1 | 9/2019 | Hansen |
| 2021/0283321 A1 | 9/2021 | Schilling et al. |

* cited by examiner

METHOD FOR MINIMIZING MISALIGNMENT NOTIFICATIONS FOR A TRANSCUTANEOUS ENERGY TRANSFER SYSTEM

This application is a continuation of U.S. patent application Ser. No. 16/816,392, filed May 12, 2020, the entire content of which is incorporated herein by reference.

FIELD

The present technology is generally related to an alert system for an implantable transcutaneous energy transfer system (TETS).

BACKGROUND

Transcutaneous energy transfer systems ("TETS") have been developed to power implantable medical devices including heart pumps such as left ventricular assist devices. A TETS may be used to supplement, replace, or charge an implanted power source, such as a rechargeable battery. The TETS can provide a variety of different implantable medical devices with continuous power delivery and/or supplemental power delivery.

Use of a TETS can eliminate the need to pass a power lead through the skin and does not require the physical power lead to chronically transverse across tissue physically connecting to the implant which is attached to the apex of the heart. This can significantly reduce the risk of infection to the patient and eliminate the discomfort from skin punctures which has been an ongoing issue for patients with percutaneous implantable medical devices.

The coupling between the external and internal coils from the TETS may vary according to the patient's physical orientation, activity, and posture which can in turn impact the delivery of power to the implanted medical device. Additionally, other power delivery variations to the implanted medical device may arise from changes in the circuit parameters, loading conditions, as well as other changes that may occur which can impact power delivery in the TETS. In order for the implanted medical device to continue functioning properly, the power delivery in the TETS must remain at a specific level to provide enough power to the implanted medical device so the life-saving function continues. When, for example, the TETS internal coil and external coil are out of alignment, the power transfer may be significantly reduced or can cease altogether. This can make it difficult or impossible to recharge an implantable battery. Additionally, the implanted medical device could cease functioning or the implanted medical device may not have adequate power to properly function.

A patient must be aware of factors that can impact the ability of the TETS to function safely and to provide a sufficient amount of energy to the implantable medical device. For example, a patient may want to know how well aligned the coils are as well as the subsequent efficiency of the energy transfer in the TETS. The regular movement of a patient can alter the position of the external coil and/or the internal coil so that the required or desired transfer of power does not take place.

Alerts may be provided if there is a misalignment of certain components within the TETS which may impact the power availability to ensure continuous power availability to the TETS. Also, when the external and internal coils are not in proper alignment, this may cause the coupling coefficient of the power transfer to be reduced and can result in the heating of the internal and/or external coils. The TETS may provide patient alerts to indicate if there is, for example, a misalignment and/or heating of the coils. However, these types of alerts can occur with a great degree of frequency based upon the movement, positioning, and repositioning of a patient which in turn can impact how energy is being transferred between the TETS and the implantable medical device. Constant alerts can be bothersome and can prevent a patient getting an appropriate amount of sleep/rest, can cause sleep deprivation, and can also be bothersome and embarrassing in various social situations where alerts are being triggered and providing interruptions. A patient may also become immune to the alerts if too many are generated and not pay attention to an alert which indicates that prompt attention is required.

SUMMARY

The techniques of this disclosure generally relate to an alert system for an implantable transcutaneous energy transfer system (TETS).

The present invention advantageously provides for a system for minimizing misalignment notifications for a transcutaneous energy transfer system ("TETS"), comprising: an implantable blood pump; an external controller having a power source and a processing circuitry; a transmission coil in communication with the external controller; a receiving coil configured for transcutaneous inductive communication with the transmission coil; and an implantable controller in communication with the receiving coil and the implantable blood pump. The implantable controller has a power source configured to receive power from the receiving coil and the processing circuitry is configured to: operate in a first mode where an alert is generated when a power efficiency transfer between the transmission coil and the receiving coil is below a first predetermined threshold; and operate in a second mode where the alert is only generated when the power remaining in the power source for the implantable controller is below a first predetermined power source threshold.

In another aspect of this embodiment, the alert is generated in the first mode after a first predetermined period of time after the power efficiency transfer between the transmission coil and the receiving coil is below the first predetermined threshold.

In another aspect of this embodiment, the alert is generated in the first mode between 2-5 minutes after the power efficiency transfer between the transmission coil and the receiving coil drop below a first predetermined threshold.

In another aspect of this embodiment, the alert is generated in the second mode after a second predetermined period of time after the first predetermined power source threshold is reached.

In another aspect of this embodiment, the alert is generated in the second mode less than 30 seconds after the first predetermined power source threshold is reached.

In another aspect of this embodiment, the second mode is configured to inhibit at least the alert of the first mode and the first mode is configured to inhibit the alert of the second mode.

In another aspect of this embodiment, the external controller further includes a display.

In another aspect of this embodiment, the display includes at least one of the group consisting of the first mode associated with the alert and the second mode associated with the alert.

In another aspect of this embodiment, at least one of the group consisting of the alert appears on the display when the first predetermined threshold is met and the alert appears on the display when the first predetermined power source threshold is met.

In another embodiment, the disclosure provides a method for minimizing misalignment notifications for a TETS, including a TETS, with an implantable blood pump, an external controller having a power source and a processing circuitry, a transmission coil in communication with the external controller, a receiving coil configured for transcutaneous inductive communication with the transmission coil, and, an implantable controller in communication with the receiving coil and the implantable blood pump. The implantable controller having a power source configured to receive power from the receiving coil. The method comprising: operating in a first mode where an alert is generated when a power efficiency transfer between the transmission coil and the receiving coil is below a first predetermined threshold; and operating in a second mode where the alert is only generated when the power remaining in the power source for the implantable controller is below a first predetermined power source threshold.

In another aspect of this embodiment, the alert in the first mode is generated after a first predetermined period of time after the power efficiency transfer between the transmission coil and the receiving coil is below the first predetermined threshold.

In another aspect of this embodiment, the first alert is generated between 2-5 minutes after the power efficiency transfer between the transmission coil and the receiving coil drop below a first predetermined threshold.

In another aspect of this embodiment, the alert is generated in the second mode after a second predetermined period of time after the first predetermined power source threshold is reached.

In another aspect of this embodiment, the alert is generated in the second mode less than 30 seconds after the first predetermined power source threshold is reached.

In another aspect of this embodiment, the alert in the first mode is disabled when the external control is configured to operate in the second mode.

In another aspect of this embodiment, the external controller further includes a display.

In another aspect of this embodiment, the display includes at least one of the group consisting of the first mode associated with the alert and the second mode associated with the alert.

In another aspect of this embodiment, at least one of the group consisting of the alert appears on the display when the first predetermined threshold is met and the alert appears on the display when the first predetermined power source threshold is met.

In another aspect of this embodiment, the processing circuitry is configured to operate in the first mode for a predetermined period of time and the processing circuitry is configured to operate in the second mode for a different predetermined period of time.

In another embodiment, a method for minimizing misalignment notifications for a TETS, including a TETS, with an implantable blood pump, an external controller having a power source and a processing circuitry, a transmission coil in communication with the external controller, a receiving coil configured for transcutaneous inductive communication with the transmission coil, and, an implantable controller in communication with the receiving coil and the implantable blood pump, and the implantable controller having a power source configured to receive power from the receiving coil. The method comprises: operating in a first mode where an alert is generated after a first predetermined period of time when a power efficiency transfer between the transmission coil and the receiving coil is below a first predetermined threshold; disabling the alert that is generated after a first predetermined period of time when a power efficiency transfer between the transmission coil and the receiving coil is below a first predetermined threshold in a second mode; and generating the alert in the second mode after a second predetermined period of time when the power remaining in the power source for the implantable controller is below a first predetermined power source threshold.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

It should be understood that various aspects disclosed herein may be combined in different combinations other than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Figure 1:
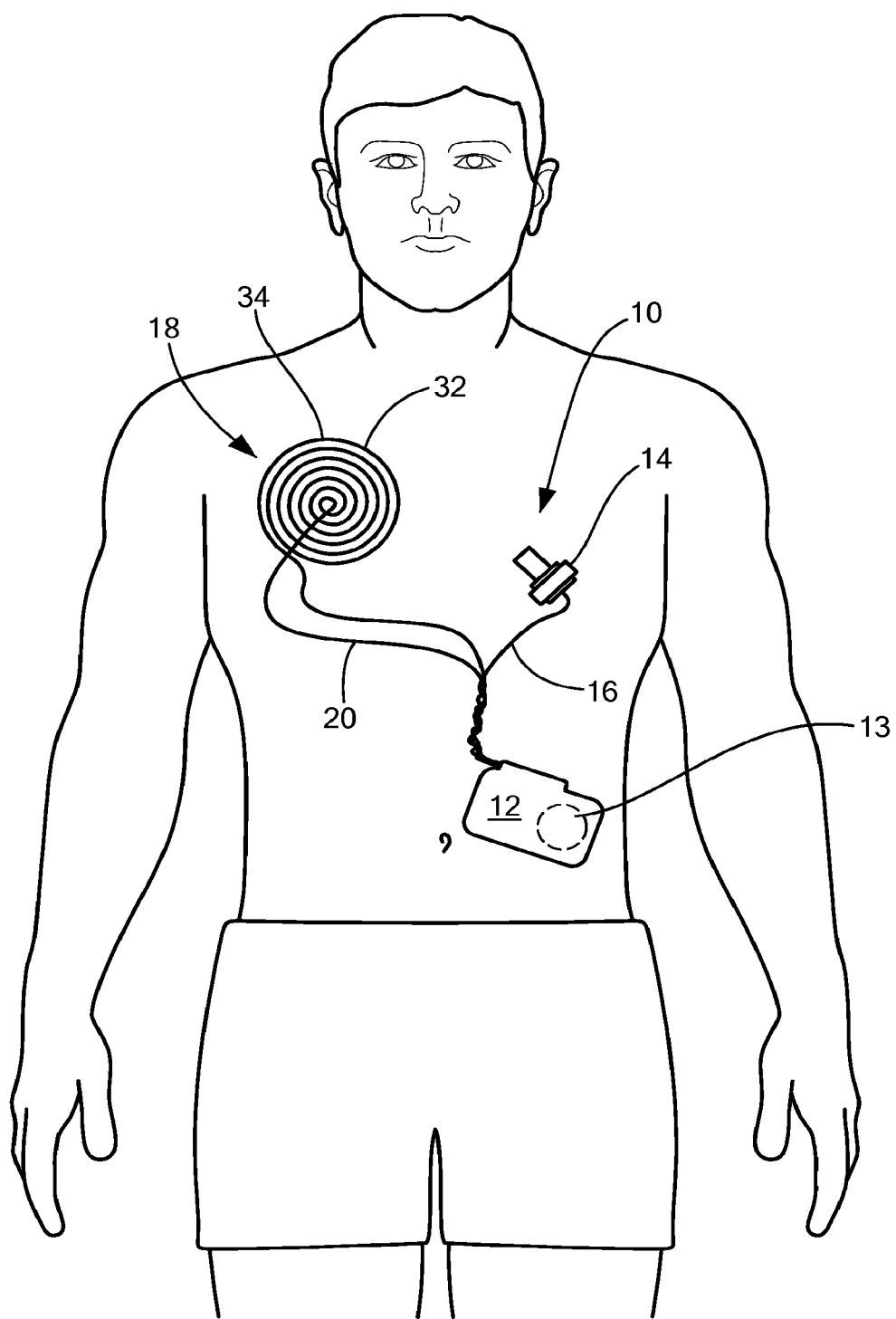
FIG. 1 is a is a front inside of the body view of a patient with a left ventricular assist device, receiving coil, and controller, fully implanted within the patient.
Figure 2:
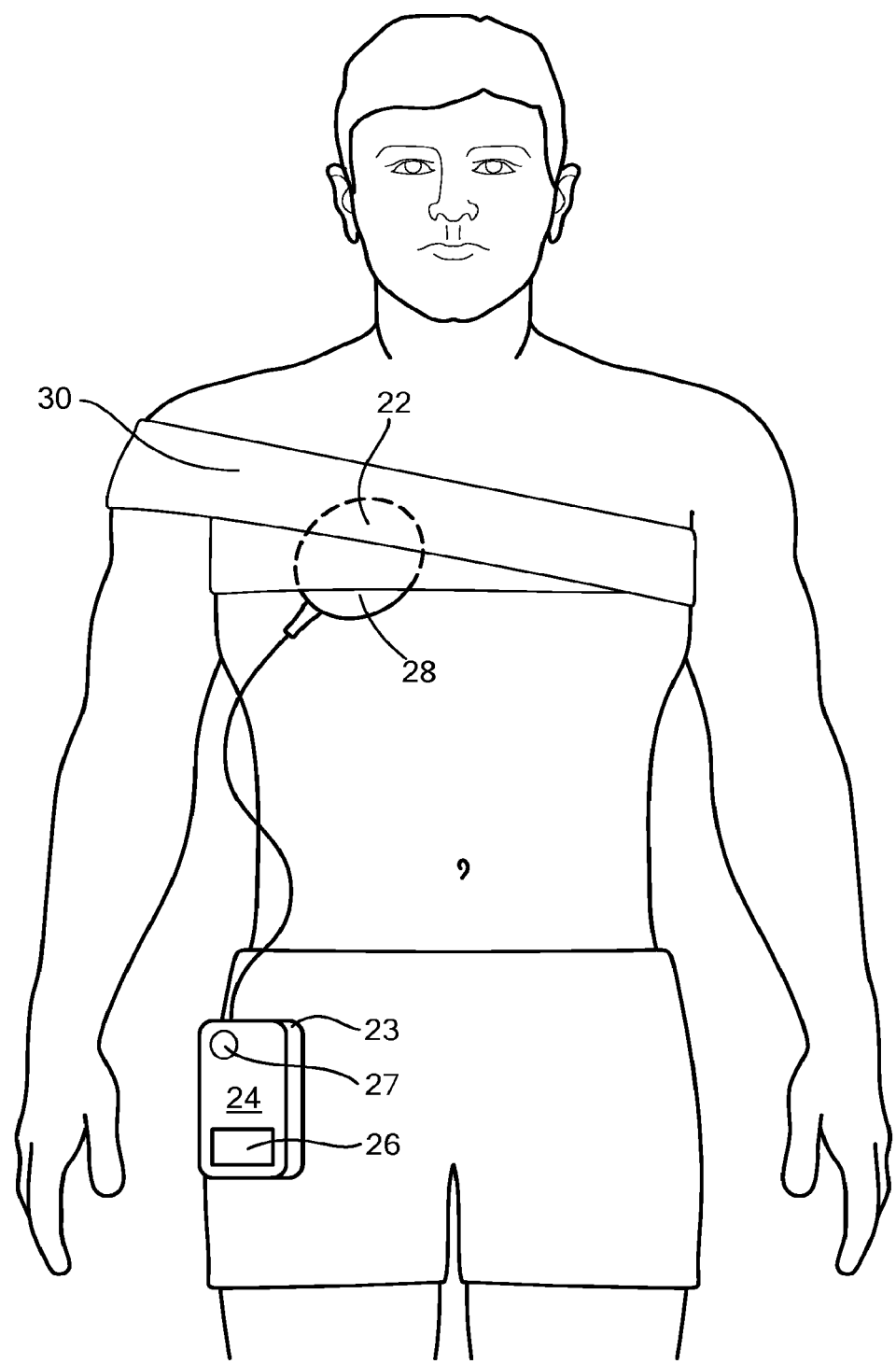
FIG. 2 is a front outside of the body view of the patient shown in FIG. 1 showing a battery and transmission coil coupled to the patient.

Referring now to the drawings in which like reference designators refer to like elements there is shown in FIGS. 1 and 2 an exemplary transcutaneous energy transfer system ("TETS") constructed in accordance with the principles of the present application and designated generally as "10." The TETS 10 may be fully implantable within a patient, whether human or animal, which is to say there are no percutaneous connections between the implanted components of the TETS 10 and the components outside of the body of the patient. In the configuration shown in FIG. 1, the TETS 10 includes an internal controller 12 implanted within the body of the patient. The internal controller 12 may include a power source 13 configured to power the components of the controller and provide power to one or more implantable medical devices, for example, an implantable blood pump such as a ventricular assist device ("VAD") 14 implanted within the left ventricle of the patient's heart. The power source 13 may include a variety of different types of power sources including an implantable battery. VADs 14 may include centrifugal pumps, axial pumps, or other kinds electromagnetic pumps configured to pump blood from the heart to blood vessels to circulate around the body. One such centrifugal pump is the HVAD sold by HeartWare, Inc. and is shown and described in U.S. Pat. No. 7,997,854, the entirety of which is incorporated by reference. One such axial pump is shown and described in U.S. Pat. No 8,419,609, the entirety of which is incorporated herein by reference. In an exemplary configuration, the VAD 14 is electrically coupled to the internal controller 12 by one or more implanted conductors 16 configured to provide power to the VAD 14, relay one or more measured feedback signals from the VAD 14, and/or provide operating instructions to the VAD 14.

Continuing to refer to FIG. 1, a receiving coil 18 may also be coupled to the internal controller 12 by, for example, one or more implanted conductors 20. In an exemplary configuration, the receiving coil 18 may be implanted subcutaneously proximate the thoracic cavity, although any subcutaneous position may be utilized for implanting the receiving coil 18. The receiving coil 18 is configured to be inductively powered through the patient's skin by a transmission coil 22 (seen in FIG. 2) disposed opposite the receiving coil 18 on the outside/exterior of the patient's body. For example, as shown in FIG. 2, a transmission coil 22 may be coupled to an external controller 23 having a power source 24, for example, a portable battery carried by the patient. In one configuration, the battery is configured to generate a radiofrequency signal for transmission of energy from the transmission coil 22 to the receiving coil 18. The receiving coil 18 may be configured for transcutaneous inductive communication with the transmission coil 22.

The external controller 23 may further include a display 26 configured to provide information to the patient in one or more ways including audibly, visually and/or tacitly. Additionally, the external controller 23 may further include processing circuitry 27 which can process and transmit information. The processing circuitry 27 may perform various simple and complex operations including, but not limited to, the amplification of signals, computations, and the movement of data from one place to another. The various simple and complex operations that may be performed by the processing circuitry 27 in the external controller 23 is discussed in more detail below with reference to FIG. 4. The processing circuitry 27 may include one or more processors and memory. The external controller 23 may further comprise software, which is stored in, for example, memory at the external controller 23, or stored in external memory (e.g., database, storage array, network storage device, etc.) accessible by the external controller 23. The software may be executable by the processing circuitry 27. The software may include a client application operable to provide a service to a human or non-human user via the external controller 23, with the support of a host computer.

Referring back to FIG. 2, the transmission coil 22 is optionally housed within sealed packaging 28 to protect the transmission coil 22 and is optionally attached to a sling 30 around the patient's torso to maintain the transmission coil 22 in a fixed position for power transmission to the receiving coil 18. Although the sling 30 is shown in FIG. 2, any fixation device may be utilized to either adhere or otherwise affix the transmission coil 22 to the skin of the patient.

Figure 3:
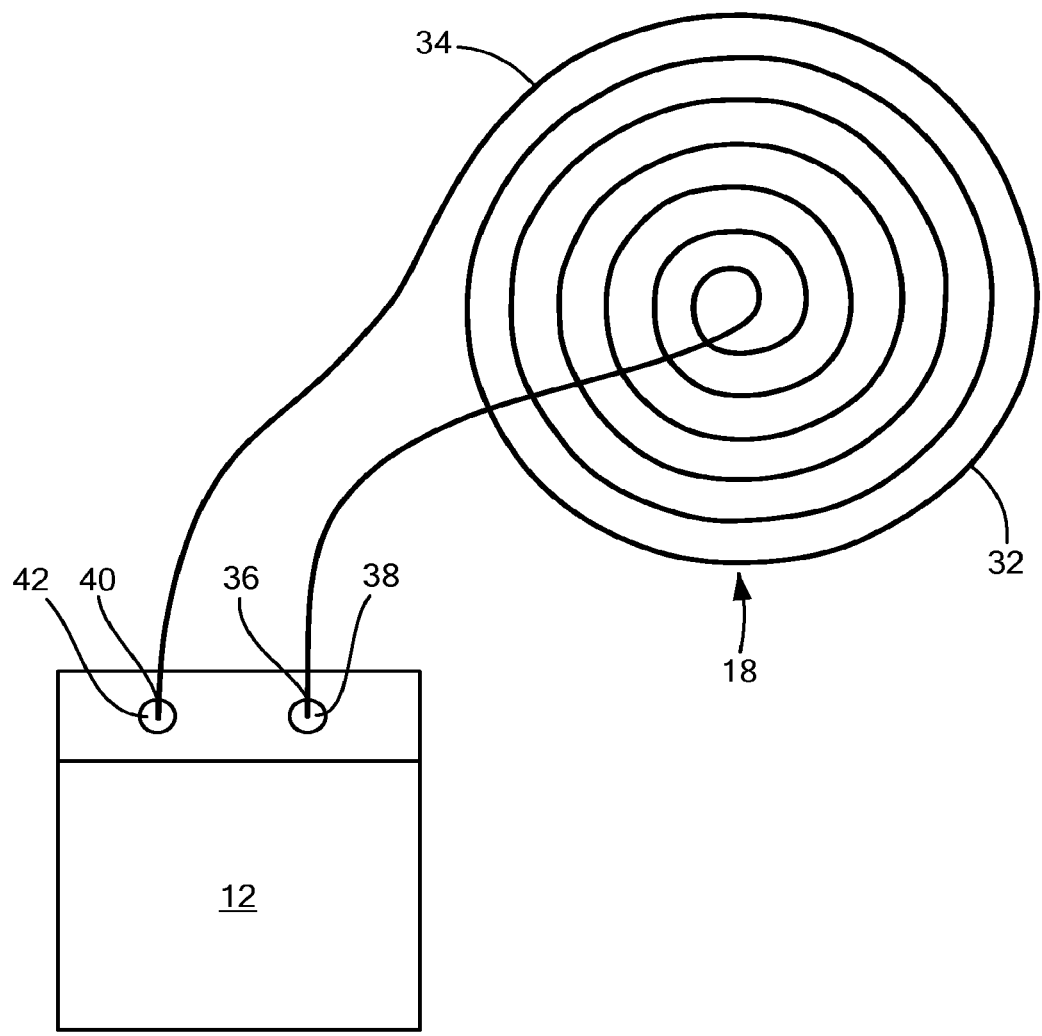
FIG. 3 is a front view of the receiving coil and controller shown in FIG. 1.

Referring now to FIGS. 1 and 3, the receiving coil 18 may include at least one conductor 32 defining a coil 34 and configured to power the VAD 14. The receiving coil 18 may be any shape or size and, for example, in one configuration, the receiving coil 18 may define a substantially planar coil defining a diameter such that is substantially co-planer with an interior surface of the dermis. The receiving coil 18 may be coupled with the internal controller 12 with a first end 36 being electrically coupled to a first coupling 38 of the internal controller 12 and a second end 40 being coupled to a second coupling 42 of the internal controller 12 such that a voltage may be applied to the coil 18. Alternatively, the receiving coil 18 may be coupled with the internal controller 12 using joints or any other configuration.

Figure 4:
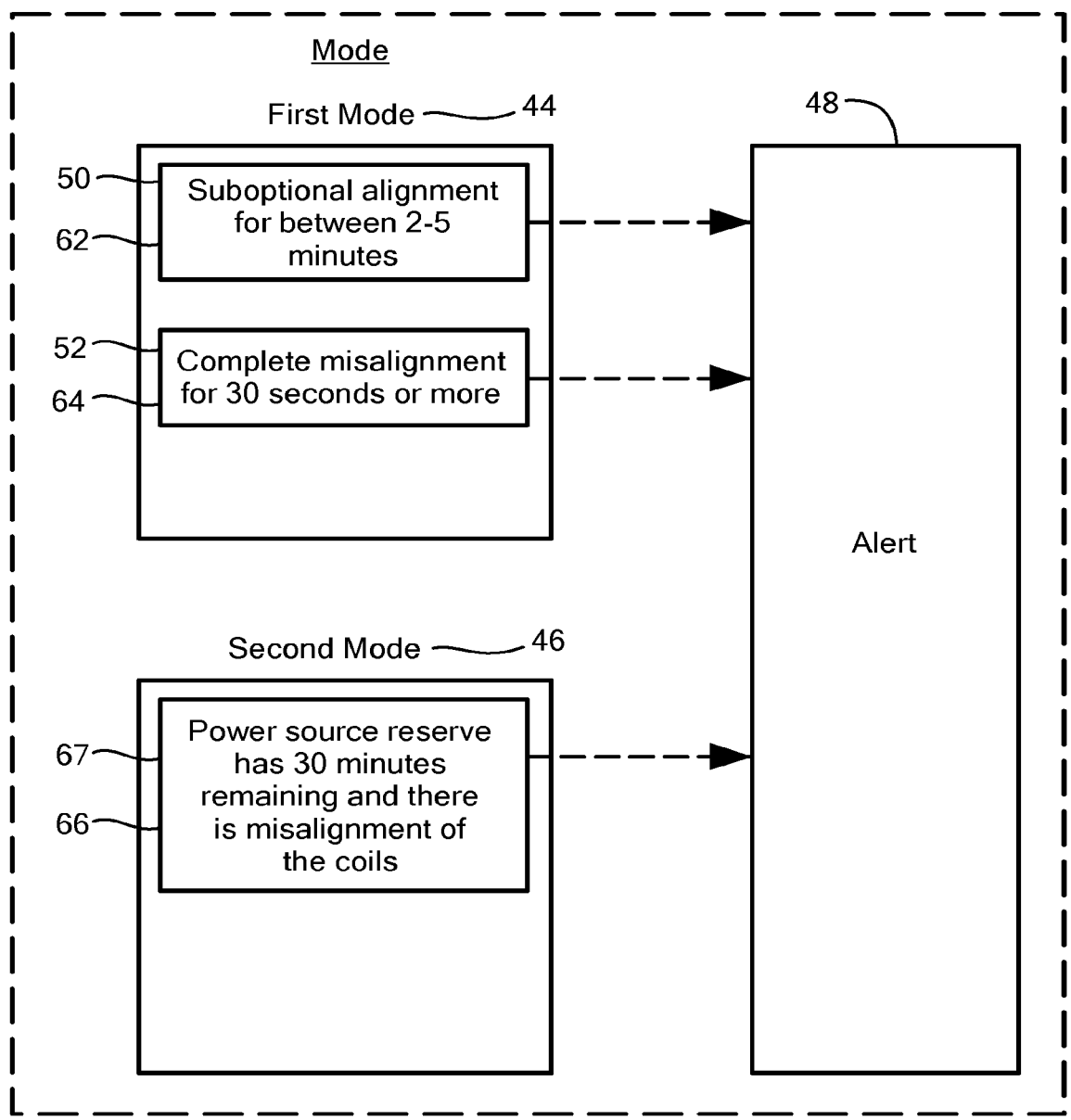
FIG. 4 is a view of operating conditions associated with the display with corresponding alerts.

Referring now to FIG. 4, the external controller 23 may generate a variety of different indicators, including alerts, which may be shown on the display 26. The display 26 may show a variety of different visual, audible, and/or tactile indicators and/or alerts. These indicators and/or alerts may be in colors including red, yellow, orange, blue, purple, pink and green on the display 26. Alternatively and/or additionally, the visual indicator may be a written alert to provide information to the patient about how the TETS is functioning and/or any required actions to keep the TETS functioning. Different alerts and/or indicators may appear together, such as a visual and audible alert, or different alerts and/or indicators may be triggered at different times. For example, a visual alert may be displayed and then after a period of time an audible alert may be heard. Alternatively, a visual alert may be displayed at the same time as an audible alert. The indicator may also be audible and loud enough so that an individual could hear the alert during the day in a noisy situation or could wake someone that is sleeping. When and how indicators appear may be preset or selected. For example, if user is going into a social situation where audible alerts may be disruptive, the visual indicator may appear on the display 26 for a period of time before an audible alert is heard.

Continuing to refer to FIG. 4, the indicators that are shown on the display may be based upon the particular mode that the external controller 23 is operating in. For example, the external controller 23 may in one mode generate a specific or particular indicator which is then communicated to the display 26 and shown on the display 26 as an alert. Alternatively, if the external controller 23 is operating in a different mode, the indicators or alerts may be inhibited and not communicated to the display 26 and/or shown on the display 26. The external controller 23 may operate in an unlimited number of different modes and each mode may configured based upon the implantable medical device that is being used as well as the requirements for the individual patient using the implantable medical device. How and when alerts and/or indicators are generated may be based upon the mode that the external controller 23 is configured in at any given time and/or the setting of the external controller 23. For example, a clinician, a patient, or another individual could set the mode that the external controller 23 is going to operate in for a particular period of time. A clinician, patient, or another individual could also disable a mode and/or change the mode at any time. The designation of the particular mode may be based on a patient's sleep and wake cycle, such that a first mode 44 may be activated while the patient is awake and a second mode 46 may be activated while the patient is asleep. As a non-limiting example, the first mode 44 may be set for a specific period of time and the second mode 46 may be set for a particular period of time which may be a different than or the same as the period of time in the first mode 44. This timing may correspond to the sleep and wake cycles of the patient. Alternatively, the TETS 10 may include sensors that can provide information about the position, posture, heart rate, and/or activity level of an individual using the TETS 10 and the information from the sensors may be used to determine if an individual is asleep or awake based upon preset parameters. These parameters may be based upon the habits and routines of the individual using the TETS 10 or the parameters may be generally programmed into the processing circuitry 27. For example, the internal controller 12 may be able to detect a patient's sleep and wake cycles based upon heart rate and an accelerometer signal. The TETS 10 may also include a button, knob, and/or switch that may be depressed or moved to change from one mode to another mode. When it is determined that a patient is awake, the first mode 44 may be activated and when it is determined that the patient is asleep the second mode 46 may be activated.

Continuing to refer to FIG. 4, when a patient is awake, the external controller 23 may be configured to operate in the first mode 44. The first mode 44 may be more sensitive to potential issues with the TETS 10 related to, for example, coil alignment, coil temperature, flow rates, and energy transfer between the coils and provide more frequent notifications and/or information to the patient about any issues related to the TETS 10. In the first mode 44, an alert 48 may be generated in situations including the following: when the power efficiency transfer between the transmission coil 22 and the receiving coil 18 drops below a certain level; when the temperature of the transmission coil 22 rises above a particular temperature; or when the internal controller 12 power demand rises above a particular level. A variety of different values for each situation may programmed into the external controller 23 and the system may generate the alert 48 based upon preset parameters. The external controller 23 may continuously and/or at preset intervals monitor the conditions of the TETS 10 and save this information so that it can later be accessed. For example, a medical provider can view the stored information to see how the TETS 10 is performing over a particular period of time to help identify any problems or issues that may arise for the particular user.

Continuing to refer to FIG. 4, the timing and frequency of when the alert 48 is generated may be based upon the mode that the external controller 23 is operating in. The first mode 44 may be enabled or activated when the patient is awake. In the first mode 44, the alert 48 may be generated when a power efficiency transfer between the transmission coil 22 and the receiving coil 18 falls below a specified level. As shown in FIG. 4, the alert 48 may appear on the display 26 after there has been suboptimal alignment of the transmission coil 22 and the receiving coil 18 for a period of time. This period of time may be for a few minutes, for example, between two (2) to five (5) minutes, after the power efficiency transfer between the transmission coil 22 and the receiving coil 18 has been below a specified level. Having a few minute delay before an alert 48 is generated may allow the transmission coil 22 and the receiving coil 18 to transiently align and realign without an alert 48 being triggered. This suboptimal alignment may cause the power efficiency transfer between the transmission coil 22 and the receiving coil 18 to fall below a particular level, which may be identified as a first predetermined threshold 50. The time period where the external controller 23 has been recognizing the suboptimal alignment before an alert 48 is generated may be identified as a first predetermined period of time 62. In the non-limiting example, the time period may be between two (2) and five (5) minutes. The settings of what defines the first predetermined threshold 50 and the first predetermined period of time 62 in the external controller 23 may be based upon the implantable device as well as the patient's needs and requirements. In this non-limiting example, the suboptimal alignment of the coils may not require an urgent and/or immediate response by the user, operator, clinician, or other person monitoring or wearing the implantable medical device. The alert 48 may indicate that an immediate response is not required and provide the user with information on the display 26, stating, for example, "suboptimal alignment" or that the "power efficiency transfer is suboptimal" or by using some other visual or graphic suggestion indicating that there is partial misalignment. If the power efficiency transfer between the transmission coil 22 and the receiving coil 18 improves and the first predetermined threshold 50 is no longer met, the alert 48 on the display 26 may, for example, state that "Reconnection has Occurred" or that "Power Efficiency Transfer is Optimal" to indicate that the issue has been resolved and no longer requires the attention of the user. The information on the display 26 may appear at the same time that an audible alert may be heard, before an audible alert, or after an audible alert. Alternatively, the alert 48 may be turned off on the display 26 once the issue has resolved.

Continuing to refer to FIG. 4, the alert 48 may also be generated when there is a complete misalignment of the transmission coil 22 and the receiving coil 18 for a specified period of time which may be identified as a second predetermined threshold 54. As a non-limiting example, the second predetermined threshold 54 may be thirty (30) seconds after the external controller 23 recognizes that there has been a complete misalignment of the coils. For example, the alert 48 may be generated when there is complete misalignment of the transmission coil 22 and the receiving coil 18 for thirty (30) seconds or more as little or no energy may be being transferred between the coils 18 and 22. This complete misalignment may require an urgent and/or immediate response by the user, operator, clinician, or other person monitoring the patient. The urgency may depend upon the status of the power source 13 at the time of the complete misalignment and whether there is a significant capacity of the power source 13 remaining. If the power source 13 has significant capacity remaining, than the urgency may be less than if there is some capacity remaining in the power source 13 and the alert 48 may be generated based upon this urgency. The alert 48 may include information on the display 26 indicating that an immediate response is required, for example, the display 26 may say "complete misalignment" or "power efficiency transfer not occurring." Another visual and/or graphic indicator may also be generated as part of the alert 48. If the power efficiency transfer between the transmission coil 22 and the receiving coil 18 improves and the second predetermined threshold 52 is no longer met, the alert 48 on the display 26 may say that "Reconnection has Occurred" or that "Power Efficiency Transfer is Optimal" to indicate that the issue has been resolved, or the alert 48 may be turned off.

Continuing to refer to situations in which the patient is awake and the external controller 23 is operating in the first mode 44, other examples (not shown) of when the alert 48 may be triggered include the generation of an alert 48 after the transmission coil 22 has reached a particular temperature for a specified period of time. For example, after the transmission coil 22 has reached a particular temperature, identified by the external controller 23 as a first predetermined transmission coil temperature 54, for between two (2) and five (5) minutes, identified as the first predetermined period of time 62, the alert 48 may be generated. The setting in the external controller 23 of what is the first predetermined transmission coil temperature 54 and the first predetermined period of time 62 may be set to any set of parameters. In the first mode 44, the first predetermined transmission coil temperature 54 may be set based upon the optimization of thermal comfort and based upon normal use of the TETS 10. The alert 48 may not require an urgent and/or immediate response. If a notification on the display 26 is provided it may indicate that there is "excess heating" or that the "the heating level of coils is suboptimal." If the condition is resolved and the transmission coil temperature cools down, the alert 48 on the display may state, for example, "Temperature Adequate" or "Coil Temperature Optimal" to indicate the resolution of the issue, or the alert 48 may be turned off.

Continuing to refer to situations in which the patient is awake and the external controller 23 is operating in the first mode 44, the alert 48 may also be generated after a shorter specified time than what is identified as the first predetermined period of time 62 after the temperature of the transmission coil 22 rises above a higher temperature than what is identified as the first predetermined transmission coil temperature 54. For example, the alert 48 may be generated after the temperature of the transmission coil 22 rises above a certain preset temperature, identified as a second predetermined transmission coil temperature, for thirty (30) seconds, identified as the second predetermined period of time 64. In this particular example, the second predetermined transmission coil temperature 56 may require an urgent and/or immediate response by the user, operator, clinician, or other person monitoring or wearing the implantable medical device so that the TETS 10 can continue to operate. The display 26 may indicate, for example, that there is "Overheating," "Attention Required, Overheating" or "Too Hot." If the temperature of the transmission coil 22 falls below the second predetermined transmission coil temperature 56, the alert 48 may indicate that, for example, "Temperature Adequate" or that "Coil Temperature Optimal" to demonstrate that the issue has been resolved and no longer requires the attention of the user, or the alert 48 may be turned off.

Continuing to refer to situations in which the patient is awake and the external controller 23 is operating in the first mode 44, the alert 48 may also be generated once the power demand of the internal controller rises above a certain level for a specified period of time As a non-limiting example, the power demand may rise to a certain level, identified as a first predetermined internal controller power demand 58, for between two (2) and five (5) minutes, identified as the first predetermined period of time 62. When the alert 48 is triggered, it may not require an immediate response and any notification on the display 26 may indicate, for example, that "excess power demand by internal controller" or "the power demand is suboptimal." If the issues resolves and the power demand falls below a certain specified level, the alert 48 on the display 26 may indicate "Power Demand Optimal" to demonstrate that the issue has been resolved and no longer requires the attention of the user, or the alert 48 may be turned off.

Continuing to refer to situations in which the patient is awake and the external controller 23 is operating in the first mode 44, the alert may also be generated after a shorter specified time than what is identified as the first predetermined period of time 62 after the power demand of the internal controller 12 rises to a higher level than what is identified as the first predetermined internal controller power demand 58. For example, the power demand may rise to a level that is higher than what was identified as the first predetermined internal controller power demand 58, identified as a second predetermined internal controller power demand 60, for thirty (30) second or more, identified as the second predetermined period of time 64. This higher power demand may require an urgent and/or immediate response by the user, operator, clinician, or other person monitoring the implantable medical device. Any notification on the display 26 may state, for example, "Power Demand Issue," "Attention Required, Power Demand Issue" or "Immediate Attention." If the power demand falls back to a level that does not require any attention, the alert 48 may change and say, for example, "Power Demand Optimal" to demonstrate that the issue has been resolved and no longer requires the attention of the user.

Continuing to refer to FIG. 4, the second mode 46 may be set to limit the number of interruptions received by the patient so that a patient can sleep, relax, or limit interruptions. For example, in a social situation, it may be desirable to have limited alerts 48 and interruptions. A patient or clinician may change the setting from the first mode 44 to the second mode 46 manually at any time, the modes may be preset to change at a particular time of the day like when the patient usually goes to sleep and remain in the second mode 46 for a set period of time thereafter, or the TETS 10 may be configured to detect when the patient is asleep or resting and change to the second mode 46. For example, a preset time may be if a patient normally goes to bed at 10:00 p.m., the second mode 46 may be set at this time and the system may remain in the second mode 46 until 6:00 a.m. Then, at 6:00 a.m., the second mode 46 may be deactivated and the first mode 44 may be activated so that the patient may receive more alerts 48 throughout the day and/or the system may generally be more sensitive/responsive to notifying the patient about misalignment conditions as well as other conditions. This timing may be preset, depending upon the schedule of the patient and when the patient would like to be in the first mode 44 or the second mode 46. Alerts 48 which may be activated in the first mode 44 may be deactivated in the second mode 46 so that the patient can rest and sleep or engage in another activity where the patient would like to minimize alerts 48 such as in a theatre, during a meeting, or in another setting. In general, if the patient operates in the second mode 46, the patient will not receive as many notifications and/or alerts 48 concerning the TETS 10. For example, the alerts 48 in the second mode 46 may only be triggered when it is necessary for safety reasons to take prompt action or attention by the patient and/or caregiver to keep the TETS 10 functioning safely and properly. In the second mode 46, certain parameters may be set in the external controller 23 such that the alert 48 may be triggered when certain conditions are met. For example, the reconnection alerts 48 may be inhibited in the second mode 46.

Continuing to refer to FIG. 4, the alert 48 may be inhibited when urgent attention is not required for the TETS 10 to continue to function. For example, the alert 48 may not be triggered when there is suboptimal alignment of the coils and a significant amount of power is remaining in the power source 13, or when the transmission coil 22 reaches a particular temperature, or when the internal controller's 12 power demand reaches a particular level. In the second mode 46, alignment related alerts 48 may be inhibited. However, when a user's more urgent attention is required based upon a particular preset parameter/condition, the alert 48 may be generated.

Continuing to refer to FIG. 4, in an exemplary embodiment, in the second mode 46, the alert 48 may be generated when the power remaining in the power source 13 in the implantable controller 12 continues to drain due to suboptimal and/or complete misalignment between the transmission coil 22 and the receiving coil 18 and causes the power remaining in the power source 13 to fall below a first predetermined power source threshold 67. The first predetermined power source threshold 67 may be set to a variety of different parameters which may indicate that the power remaining in the power source 13 is low and that there is some misalignment between the transmission coil 22 and the receiving coil 18. When the power level of the power source 13 is continually being drained over a period of time, there may only be a certain amount of energy in reserve in the power source 13 and the reserve may only be able to power the power source 13 for a certain period of time, identified as a third predetermined period of time 66. For example, the alert 48 may be activated when there is suboptimal and/or complete misalignment between the transmission coil 22 and the receiving coil 18 which drains the power in the power source 13 and once the power source 13 reserve only has thirty (30) minutes remaining. In alternate embodiments, in the second mode 46, the alert 48 be generated after the power efficiency transfer between the transmission coil 22 and the receiving coil 18 falls below a particular level, which may be identified as the first predetermined threshold 50 and/or the second predetermined threshold 54. Also, the alert 48 in the second mode 46 may be triggered after first predetermined threshold 50 and/or second predetermined threshold 52 have been met for either the first predetermined period of time 62 and/or the second predetermined period of time 64. In another embodiment, the alert 48 may be triggered when only thirty (30) minutes of power remains in the reserve of the power source 13 and this may be related and/or unrelated to any misalignment of the transmission coil 22 and the receiving coil 18. Additionally, other combinations of preset parameters may be used to trigger an alert 48 in the second mode 46 when more urgent attention is required. Since the triggering of the alert 48 in the second mode 46 may require a more urgent and/or immediate response, any notification on the display 26 may indicate that an immediate response is required like "30 minute warning" and/or "power efficiency transfer not occurring." If the power efficiency transfer between the transmission coil 22 and the receiving coil 18 rises above a particular level and/or the preset parameter that triggered the alert 48 is resolved, the alert 48 may be deactivated.

Although not shown, in the second mode 46, the alert 48 may also be generated after a specified transmission coil 22 temperature is met or after the power demand of the internal controller 12 rises above a particular level which requires more urgent attention. In the second mode 46, the specified transmission coil 22 temperature may be higher than the first predetermined transmission coil temperature 54 and/or the second predetermined transmission coil temperature 56 such that in the second mode 46 there will be less alerts 48 or notifications. Any notification on the display 26 may indicate that an immediate response is required and state, for example, "Overheating," "Attention Required, Overheating" or "Too Hot." Once the issue is resolved, the alert 48 may be deactivated. In the second mode 46, while alerts 48 may be less frequent than in the first mode 44, the current alignment status of the coils may still be displayed on the power transmitter and the logging of data may still continue. While the example in FIG. 4 only shows the alert 48 being triggered in relation to certain pre-set conditions, any number of different alerts can occur at different times depending upon the parameters set in the external controller 23. In the second mode 46, the alert 48 for the misalignment may be inhibited, as long as no other alert 48 conditions are present.

In both the second mode 46 and the first mode 44, if the TETS 10 experiences a non-transient loss of Bluetooth communication or the loss of another type of short-range wireless communication between the internal controller 12 and the external controller 23, an alert 48 may be generated to indicate this loss of connectivity. This alert 48 may be generated after a preset or predetermined period of time after the loss of connectivity or the alert 48 may be generated immediately after the loss of connectivity is detected. The preset or predetermined period of time may be the same in both the first mode 44 and the second mode 46 or different in the first mode 44 and the second mode 46. This period of time may be short to alert the user so that the connectivity can be reestablished and alerts 48 can be provided. Alerts 48 which may be generated after this loss of short-range wireless communication, may come from the internal components of the TETS 10 because of the loss of connectivity.

Continuing to refer to FIG. 4, the external controller 23 may also operate in a third mode 68 (not shown). The third mode 68 may be where the user is operating off the power source 13 in the controller 12 and no power is being delivered from the power source 24 in the external controller 23. For example, the patient may not be wearing any TETS 10 charging equipment and may only be using the power source 13 in the internal controller 12. Certain preset parameters may be set in the third mode 68 such as a predetermined internal controller 12 power demand which may trigger an alert 48. In the third mode 68, there may be no alerts 48 for alignment issues as the patient may not be using the transmission coil 22. The TETS 10 may be configured to operate in a number of different modes.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A system comprising:
a transcutaneous energy transfer system ("TETS") comprising a receiving coil configured for transcutaneous inductive communication with a transmission coil; and
processing circuitry configured to:
generate a first alert in response to:
the processing circuitry operating in a first mode for notifying a user of a misalignment condition, and
a temperature of the transmission coil exceeding a first temperature threshold; and
generate a second alert in response to:
the processing circuitry operating in a second mode for notifying the user of the misalignment condition, wherein the second mode has a lower sensitivity relative to the first mode, and
the temperature of the transmission coil exceeding a second temperature threshold, wherein the second temperature threshold is greater than the first temperature threshold.

2. The system of claim 1, wherein the processing circuitry is configured to generate the first alert in response to the processing circuitry operating in the first mode and the temperature of the transmission coil exceeding the first temperature threshold for a first predetermined period of time.

3. The system of claim 2, wherein the processing circuitry is configured to generate the second alert in response to the processing circuitry operating in the second mode and the temperature of the transmission coil exceeding the second temperature threshold for a second predetermined period of time.

4. The system of claim 1, wherein the processing circuitry is configured to:
operate in the first mode during a wake cycle of a user of the TETS; and
operate in the second mode during a sleep cycle of the user of the TETS.

5. The system of claim 4, wherein the processing circuitry is configured to: detect at least one of the wake cycle or the sleep cycle of the user of the TETS based upon at least one of a position, a posture, a heart rate, or an activity level of the user of the TETS.

6. The system of claim 4, wherein the processing circuitry is configured to detect at least one of the wake cycle or the sleep cycle of the user of the TETS based upon preset parameters for at least one of a position, a posture, a heart rate, or an activity level of the user of the TETS.

7. The system of claim 1, wherein the processing circuitry is configured to operate in the first mode during a first time period of a day that is associated with a wake cycle of a user of the TETS.

8. The system of claim 1, wherein the processing circuitry is configured to operate in the second mode during a second time period of a day that is associated with a sleep cycle of a user of the TETS.

9. The system of claim 1, wherein the TETS further comprises the transmission coil, and wherein the system further comprises:
an implantable blood pump; and
an external controller comprising a second power source and the processing circuitry, wherein the transmission coil is in communication with the external controller.

10. The system of claim 9, wherein the external controller further comprises a display.

11. The system of claim 10, wherein the processing circuitry is configured to:
responsive to generation of the first alert, display, via the display, a first notification indicating excessive heating of the transmission coil; and
responsive to generation of the second alert,
display, via the display, a second notification indicating that the transmission coil requires attention, and
output audio associated with the second alert.

12. A method for controlling processing circuitry of a system, the method comprising:
generating, by the processing circuitry of the system, a first alert in response to;
the processing circuitry operating in a first mode for notifying a user of a misalignment condition, and
a temperature of a transmission coil exceeding a first temperature threshold, wherein the transmission coil is in transcutaneous inductive communication with a receiving coil of a transcutaneous energy transfer system ("TETS") of the system; and
generating, by the processing circuitry, a second alert in response to:
the processing circuitry operating in a second mode for notifying the user of the misalignment condition, wherein the second mode has a lower sensitivity relative to the first mode, and
the temperature of the transmission coil exceeding a second temperature threshold, wherein the second temperature threshold is greater than the first temperature threshold.

13. The method of claim 12, wherein generating the first alert further comprises generating, by the processing circuitry, the first alert in response to the processing circuitry operating in the first mode and the temperature of the transmission coil exceeding the first temperature threshold for a first predetermined period of time.

14. The method of claim 13, wherein generating the second alert further comprises generating, by the processing circuitry, the second alert in response to the processing circuitry operating in the second mode and the temperature of the transmission coil exceeding the second temperature threshold for a second predetermined period of time.

15. The method of claim 12, further comprising:
operating, by the processing circuitry, in the first mode during a wake cycle of a user of the TETS; and
operating, by the processing circuitry, in the second mode during a sleep cycle of the user of the TETS.

16. The method of claim 15, further comprising detecting, by the processing circuitry, at least one of the wake cycle or the sleep cycle of the user of the TETS based upon at least one of a position, a posture, a heart rate, or an activity level of the user of the TETS.

17. The method of claim 15, wherein the processing circuitry is configured to detect at least one of the wake cycle or the sleep cycle of the user of the TETS based upon preset parameters for at least one of a position, a posture, a heart rate, or an activity level of the user of the TETS.

18. The method of claim 12, further comprising operating, by the processing circuitry, in the first mode during a first time period of a day that is associated with a wake cycle of a user of the TETS.

19. The method of claim 12, further comprising operating, by the processing circuitry, in the second mode during a second time period of a day that is associated with a sleep cycle of a user of the TETS.

20. The method of claim 19, further comprising:
responsive to generation of the first alert, displaying, by the processing circuitry and via the display, a first notification indicating excessive heating of the transmission coil; and
responsive to generation of the second alert,
  displaying, by the processing circuitry and via the display, a second notification indicating that the transmission coil requires attention, and
  outputting, by the processing circuitry, audio associated with the second alert. alert.

* * * * *